United States Patent [19]
Nakisher et al.

[11] Patent Number: 5,586,883
[45] Date of Patent: Dec. 24, 1996

[54] GOLD-PLATED DENTAL MATRIX BAND

[76] Inventors: Robert G. Nakisher, 1212 N. LaSalle #1301, Chicago, Ill. 60610; Daniel Uditsky, 1516 E. Flemming Dr. N., Arlington Heights, Ill. 60004

[21] Appl. No.: 398,540

[22] Filed: Mar. 6, 1995

[51] Int. Cl.⁶ ..................................................... A61C 5/04
[52] U.S. Cl. ............................................................. 433/39
[58] Field of Search ................................... 433/39, 40, 47

[56] References Cited

U.S. PATENT DOCUMENTS

| | | | |
|---|---|---|---|
| 346,082 | 7/1886 | Brophy | 433/39 |
| 3,513,545 | 5/1970 | Miller | 433/23 |
| 3,981,723 | 9/1976 | Tuccillo | 433/207 |
| 4,050,156 | 9/1977 | Chasanoff et al. | |
| 4,132,830 | 1/1979 | Tsai | 428/450 |
| 4,218,244 | 8/1980 | Knosp | 433/207 |
| 4,536,155 | 8/1985 | Ireland | 433/39 |
| 4,591,483 | 5/1986 | Nawaz | 420/463 |
| 4,704,087 | 11/1987 | Dragon | 433/39 |
| 4,804,517 | 2/1989 | Schaffer et al. | 420/587 |
| 4,943,483 | 7/1990 | Ingersoll et al. | 428/433 |
| 4,997,367 | 3/1991 | Kassel | 433/39 |
| 4,997,723 | 3/1991 | Tanaka | 428/606 |
| 5,174,954 | 12/1992 | Schaffer et al. | 420/463 |
| 5,221,207 | 6/1993 | Schoeck et al. | 433/207 |
| 5,298,218 | 3/1994 | Groll et al. | 420/463 |
| 5,338,378 | 8/1994 | Ohta et al. | 148/405 |
| 5,380,198 | 1/1995 | Suthonen | 433/39 |

*Primary Examiner*—Cary E. O'Connor
*Attorney, Agent, or Firm*—Howard & Howard

[57] ABSTRACT

A dental matrix band for use especially with modern restorative material includes a layer of gold disposed on the body portion of the matrix band. The layer of gold prevents otherwise undesirable adhesion between the restorative material and the matrix band. In the preferred embodiment, the layer of gold is plated onto a stainless steel matrix band body portion. The gold layer preferably has a thickness in the range from approximately 0.000005 inches to 0.001 inches.

17 Claims, 1 Drawing Sheet

GOLD-PLATED DENTAL MATRIX BAND

BACKGROUND OF THE INVENTION

1. Field of the Invention

This invention relates generally to dental matrix bands and, more particularly, to an improved matrix band that is useful with modern restorative materials for filling or repairing teeth.

2. Description of the Prior Art

Matrix bands are widely used by dentists while filling cavities on any of the vertical surfaces of a tooth. Matrix bands are typically made like the well-known Tofflemire design. Typical matrix bands are formed of thin, foil-like metal having the characteristics of stainless steel. A matrix band is typically wrapped around the tooth to be repaired and held in place using a conventional retainer appliance. The matrix band facilitates maintaining the restorative material in the cavity until the material cures. The matrix band is removed from about the tooth once the restorative material is set.

In modern dental applications, new restorative materials are used for restoring teeth or filling cavities. These new materials include bonded amalgam alloys and composite resins that bond to the tooth through micromechanical or chemical retention. The advantage to such materials is that a more retentive tooth repair is accomplished. A major disadvantage in using these new materials is that a conventional matrix band, which is typically made of stainless steel, has a tendency to bond to the restorative material undesirably. This bonding between a conventional matrix band and such new materials is a considerable drawback. If the restorative material adheres to the matrix band, the matrix band may be undesirably affixed to the restored tooth or removal of the matrix band results in removing the newly placed filling, also. Therefore, any bonding between the matrix band and the restorative material is highly undesirable.

Dentists have made several ad hoc attempts at preventing the undesirable bonding between such new materials and matrix bands. Currently, dentists use items such as wax, petroleum jelly, cavity varnish or mineral oil placed upon the matrix band in an attempt to prevent the bonding material from adhering to the matrix band. Using such items or materials is less than desirable because such materials may leave a residue on the tooth thereby preventing an optimum bond between the restorative material and the tooth. These materials may also increase the thickness of the matrix band, thereby making it more difficult to work with. Moreover, in some cases, the added material ruins the matrix band.

Accordingly, it is desirable to provide a matrix band that is useful in tooth restoration applications that does not have a tendency to adhere or bond to modern day restorative materials. This invention provides such a matrix band.

SUMMARY OF THE INVENTION

In most general terms, this invention provides a dental matrix band that includes a body portion having a central tooth circumscribing portion extending between and merging with a pair of arms. The arms are adapted to generally surround a preselected tooth that is to be repaired. A layer of gold is disposed upon the body portion such that the layer of gold extends over the central tooth circumscribing portion.

In a preferred embodiment, the matrix band body portion is made from stainless steel and the layer of gold is plated on the body portion. In the most preferred embodiment, the gold layer is made up of 24 karat gold and the layer of gold has a thickness in the range between about 0.000005 and 0.001 inches.

A matrix band designed in accordance with this invention provides a dentist with the ability to use a matrix band in conjunction with modern restorative materials while avoiding the shortcomings and drawbacks discussed above. Further objects and advantages and features of this invention will become apparent to those skilled in the art from the following detailed description of the preferred embodiments.

DETAILED DESCRIPTION OF THE PREFERRED EMBODIMENTS

Figure 1:
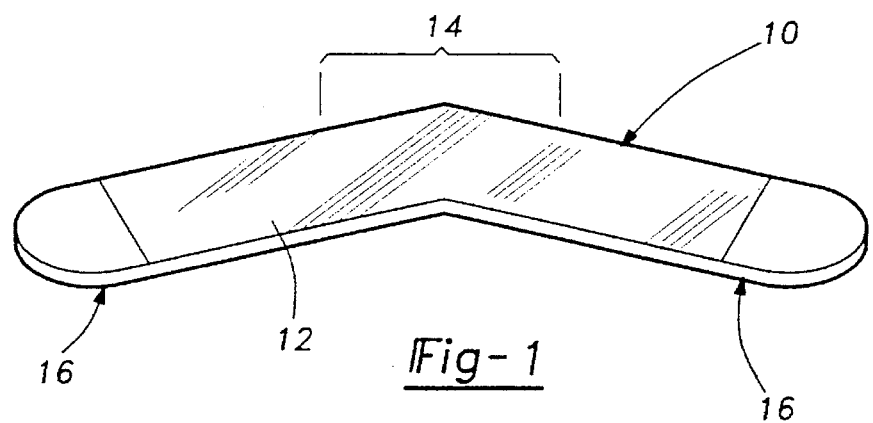
FIG. 1 shows a first preferred embodiment of a matrix band designed in accordance with this invention.
Figure 2:
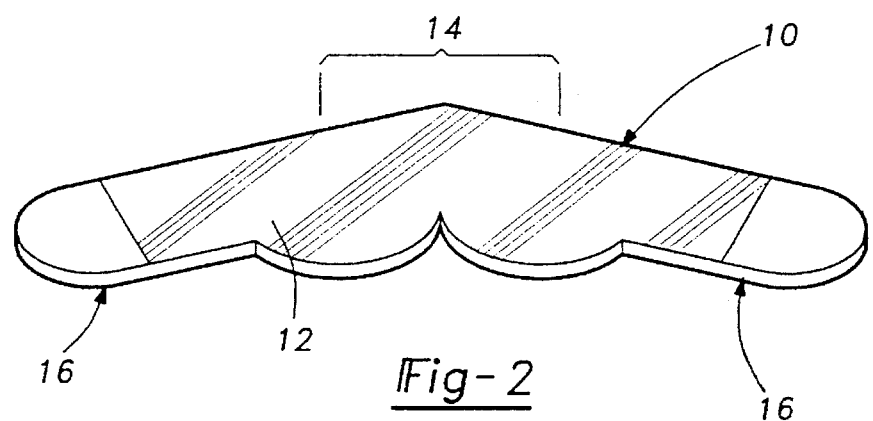
FIG. 2 illustrates a second preferred embodiment of a matrix band designed in accordance with this invention.

FIG. 1 and FIG. 2 illustrate alternative embodiments of a matrix band 10 designed in accordance with this invention. Matrix band 10 includes a layer of gold 12 disposed on the body portion of matrix band 10. The embodiment of FIG. 1 shows layer of gold 12 disposed on the entire matrix band 10. In the alternative embodiment illustrated in FIG. 2, layer of gold 12 is disposed on the central tooth circumscribing portion 14 and preferably a portion of linearly extending arms 16. Matrix band 10 has a body portion that is generally designed in accordance with the well-known Tofflemire design and it is preferably made of a foil-like material. In the most preferred embodiment, the body portion of matrix band 10 is made out of stainless steel.

Figure 3:
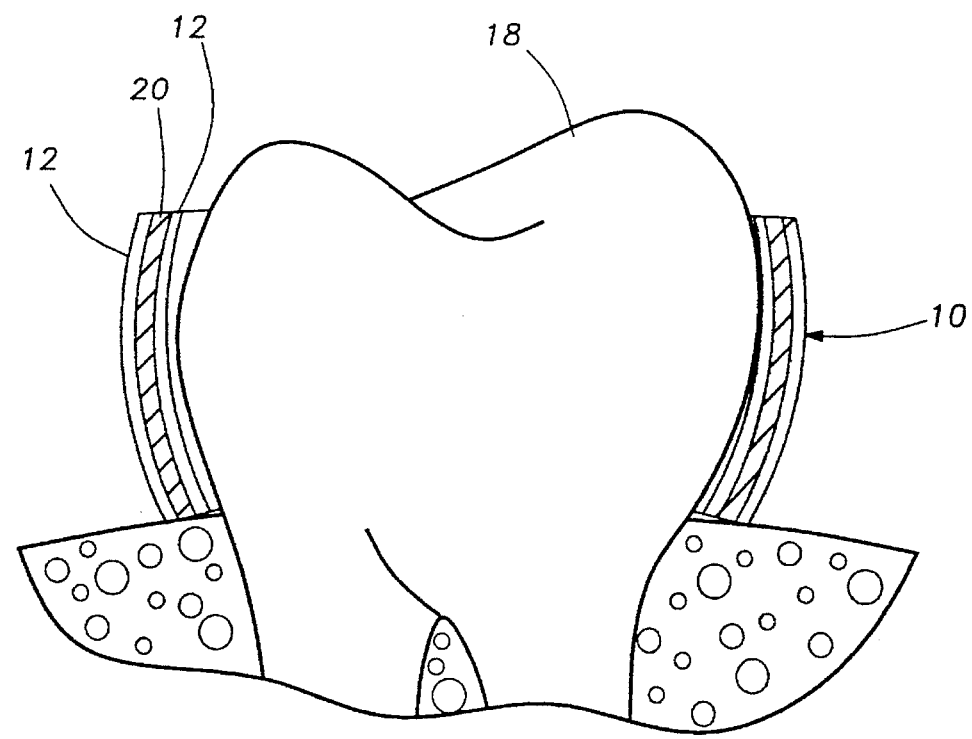
FIG. 3 is a partial cross-sectional view of a matrix band designed in accordance with this invention shown in position about a tooth.

FIG. 3 illustrates matrix band 10 in partial cross-sectional view surrounding a tooth 18. The embodiment of matrix band 10 illustrated in FIG. 3 includes a layer of gold 12 on two sides of matrix band 10. One side of matrix band 10 faces inward toward tooth 18 while the other side faces outward (i.e., away from tooth 18). The cross-hatched region 20 represents the stainless steel body portion of matrix band 10. The most preferred embodiment of this invention includes a layer of gold 12 disposed on each side of matrix band 10 as illustrated in FIG. 3. Alternatively, only one side of matrix band 10 can be plated with gold. In this alternative embodiment, it is important that a dentist be aware of which side of the band includes the gold such that the proper side is placed toward the tooth, and, therefore, toward the restorative material.

The body portion of matrix band 10 will generally have dimensions in the range of approximately 65 mm long (left to right in the drawings) by 10 mm high (top to bottom in the drawings) and a thickness in the range of 0.001 to 0.002 inches. The thickness of the layer of gold 12 disposed on the body portion of matrix band 10 is determined by the following criteria. First, the band must remain flexible such that it can be used in a way that is consistent with conventional matrix bands. Second, the thickness of the layer of gold 12 must not be appreciable. That is, the layer of gold should not increase the thickness of the matrix band by more than approximately 0.0001 inches. Third, the gold should not be worn through if burnished with a smooth metal object. This is important because of the use of dental instruments during a tooth restoration procedure. The underlying surface, that is the stainless steel of matrix band 10, should not be exposed if the band is bent once or twice. This is important because, in manipulating a matrix band in order to place it about a tooth, the band is often flexed and relaxed then flexed again before it is placed about the tooth. In the most preferred embodiment, the layer of gold 12 should remain after being exposed to high temperatures and/or pressurized steam. Typical temperatures that matrix band 10 may be exposed to during a tooth restoration procedure would be in the range from 300 degrees F. to 450 degrees F. Typical steam pressures encountered range from approximately 30 psi to 1 atm.

The thickness of the gold layer 12 is preferably in the range from approximately 0.000005 inches to 0.001 inches. In the most preferred embodiment, the layer of gold 12 is plated directly onto a stainless steel body portion of matrix band 10. The gold can also be plated directly onto the body portion of matrix band 10.

Gold is the preferred material to be disposed on the body portion of matrix band 10 because polished gold is recognized as a poor bond acceptor. Therefore, in using modern restorative materials such as amalgam bonding agents and composite resins, there is less likelihood that a matrix band coated with gold will bond to those materials. The high bond strength of the modern restorative material requires a barrier between the conventional stainless steel matrix band and the bonding agent. This invention includes the realization that gold works well for such an application.

Further, the use of gold in accordance with this invention is advantageous because of its hypoallergenic qualities. Gold is much less likely to cause an allergic reaction than stainless steel, which is comprised mostly of nickel, a common allergen.

The preferred method of applying the gold to the matrix band is using plating because no nickel or other metal need be introduced between the gold and the stainless steel matrix band. Although the preferred embodiment includes using 24 karat gold as gold layer 12, it is also within the scope of this invention to utilize other noble metals or gold alloyed with copper, silver or platium, for example, in order to increase the strength and/or hardness of the layer of gold 12. Alternative methods of disposing layer of gold 12 on the body portion of matrix 10 includes cladding the stainless steel matrix band by rolling, soldering or braising a thin sheet or leaf of gold to the body portion base metal in a conventional manner.

Variations and modification to the preferred embodiments described above are possible that do not depart from the purview and spirit of this invention. The scope of this invention is to be limited only by the following claims and all fair, legal equivalents thereof.

We claim:

1. A dental matrix band, comprising:

a body portion that is made from a foil-like metal have a central tooth circumscribing portion extending between and merging with a pair of arms adapted to generally surround a pre-selected tooth; and a layer of gold disposed on said body portion such that said layer of gold extends over said central tooth circumscribing portion.

2. The matrix band of claim 1, wherein said body portion is made from stainless steel.

3. The matrix band of claim 1, wherein said layer of gold is plated on said body portion.

4. The matrix band of claim 3, wherein said layer of gold comprises 24 carat gold.

5. The matrix band of claim 1, wherein said layer of gold has a thickness in the range between about 0.000005 and 0.001 inches.

6. The matrix band of claim 1, wherein said layer of gold is about 0.001 inches thick.

7. The matrix band of claim 1, wherein said body portion has a first side that faces said preselected tooth when said band is in use for repairing said tooth and a second side that faces away from said tooth when said band is in use and wherein said layer of gold is disposed on said first side of said body portion.

8. The matrix band of claim 7, wherein said layer of gold is also disposed on said second side of said body portion.

9. The matrix band of claim 1, wherein said pair of arms have a length and said layer of gold extends over a portion of the length of each of said arms.

10. The matrix band of claim 1, wherein said layer of gold is electroplated on said body portion.

11. The matrix band of claim 10, wherein said layer of gold comprises 24 carat gold.

12. The matrix band of claim 1, wherein said layer of gold is disposed upon the entire said body portion.

13. A dental matrix band, comprising:

a body portion having two sides and a central tooth circumscribing portion extending between and merging with a pair of arms adapted to generally surround a preselected tooth; and a layer of gold disposed on one side of said body portion such that said layer of gold extends over the entire said central tooth circumscribing portion.

14. The matrix band of claim 13, wherein said layer of gold is disposed on said two sides of said body portion.

15. The matrix band of claim 13, wherein said layer of gold is disposed upon the entire said body portion.

16. The matrix band of claim 15, wherein said layer of gold is disposed on said two sides of said body portion.

17. A dental matrix band, comprising a body portion that is made from stainless steel having a central tooth circumscribing portion extending between and merging with a pair of arms adapted to generally surround a pre-selected tooth; and a layer of gold disposed on said body portion such that said layer of gold extends over said central tooth circumscribing portion.

\* \* \* \* \*